US006194553B1

(12) United States Patent
Lee et al.

(10) Patent No.: US 6,194,553 B1
(45) Date of Patent: Feb. 27, 2001

(54) PURIFICATION OF ALPHA-1 PROTEINASE INHIBITOR

(75) Inventors: Vivian W. Lee, Alamo; Kris P. Antonsen, Berkeley, both of CA (US)

(73) Assignee: PPL Therapeutics (Scotland) Limited, Edinburgh (GB)

( * ) Notice: Subject to any disclaimer, the term of this patent is extended or adjusted under 35 U.S.C. 154(b) by 0 days.

(21) Appl. No.: 09/036,796

(22) Filed: Mar. 9, 1998

Related U.S. Application Data

(63) Continuation of application No. PCT/GB96/02194, filed on Sep. 6, 1996, now abandoned, which is a continuation of application No. 08/525,359, filed on Sep. 7, 1995, now abandoned.

(51) Int. Cl.$^7$ ............................. C07K 1/18; C07K 1/22
(52) U.S. Cl. ..................... 530/413; 530/416; 530/350; 800/7; 800/8; 800/16; 800/13; 800/14
(58) Field of Search ................ 800/8, 9, 16, 713, 800/14; 530/350, 413, 416

(56) References Cited

U.S. PATENT DOCUMENTS

| | | | |
|---|---|---|---|
| 3,293,236 | 12/1966 | Schultze et al. | 260/112 |
| 4,629,567 | 12/1986 | Bollen et al. | 210/635 |
| 5,136,025 | * 8/1992 | Scheuermann et al. | 530/413 |
| 5,476,995 | * 12/1995 | Clark et al. | 800/8 |
| 5,545,808 | * 8/1996 | Hew et al. | 800/8 |
| 5,610,285 | * 3/1997 | Lebing et al. | 530/416 |
| 5,855,883 | * 1/1999 | Khandke et al. | 424/94.62 |

FOREIGN PATENT DOCUMENTS

| | | |
|---|---|---|
| 0 698 615 A1 | 2/1996 | (EP) . |
| WO 95/35306 | 12/1995 | (WO) . |

OTHER PUBLICATIONS

Salter et al. Transgenic Chickens: Insertion of Retroviral Genes into the Chicken Germ Line. Virology, vol. 157, pp. 236–240, 1987.*
Houdebine, L.M. Production of Pharmaceutical Proteins from Transgenic Animals. Journal of Biotechnology, vol. 34, pp. 269–287, 1994.*
Wright et al. Protein Separation from Transgenic Milk. Journal of Chemical Technology and Biotechnology, vol. 59, p. 110, 1994.*
Antonsen, K.P., et al., "Elution Conditions and Degradation Mechanisms in Long–Term Immunoadsorbent Use," *Biotechnol. Prog.* 7:159–172 (Apr. 1991).
Antonsen, K.P., et al., "Controlled Release of Proteins from 2–Hydroxyethyl Methacrylate Copolymer Gels," *Biomat.. Art. Cells & Immob. Biotech.* 21:1–22 (1993).
Ballieux, B.E.P.B., et al., "Isolation of a protein complex from purulent sputum consisting of proteinase–3 and $\alpha_1 0$–antitrypsin reactive with anti neutrophil cytoplasmic antibodies," *J. Immun. Meth.* 159:63–70 (Feb. 1993).

Bischoff, R., et al., "Purification and Biochemical Characterization of Recombinant $\alpha_1$–Antitrypsin Variants Expressed in *Escherichia coli*," *Biochem.* 30:3464–3472 (Apr. 1991).
Courtney, M. et al., "High–level production of biologically active human $\alpha_1$–antitrypsin in *Escherichia coli*," *Proc. Natl. Acad. Sci. USA* 81:669–673 (Feb. 1984).
Glaser, C.B., et al., "Low pH stability of alpha–1–antitrypsin," *Biochim. Biophys. Acta* 491:325–330 (Mar. 1977).
Hanson, L.A., and Johansson, B.G., "Immunological Studies of Milk," *Milk Proteins chemistry and molecular biology*. vol. 1, McKenzie, H.A., ed., Academic Press, New York, pp. 45–123 (1970).
Hoylaerts, M., et al., "High–level production and isolation of human recombinant $\alpha_1$–proteinase inhibitor in yeast," *FEBS Lett.* 204:83–87 (Aug. 1986).
Jenness, R., "Protein Composition of Milk," in *Milk Proteins chemistry and molecular biology, vol. 1*, McKenzie, H.A., ed., Academic Press, New York, pp. 17–43 (1970).
Kurecki, T., et al., "Purification of Human Plasma $\alpha_2$Macroglobul in and $\alpha_1$ Proteinase Inhibitor Using Zinc Chelate Chromatography," *Analyt. Biochem.* 99:415–420 (Nov. 1979).
Mistry, R., et al. "Isolation and characterization of sheep $\alpha_1$–proteinase inhibitor," *Biochem. J.* 273:685–690 (Feb. 1991).
Sleep, D., et al., "*Saccharomyces cerevisiae* Strains That Overexpress Heterologous Proteins," *Bio/Tech.* 9:183–187 (Feb. 1991).
Sulkowski, E., "The Saga of IMAC and MIT," *BioEssays* 10:170–175 (May 1989).
Wilkins, T.D., and Velander, W., "Isolation of Recombinant Proteins From Milk," *J. Cell. Biochem.* 49:333–338 (Aug. 1992).
Wright, G., et al., "High level Expression of Active Human Alpha–1–Antitrypsin in the Milk of Transgenic Sheep," *Bio/Tech.* 9:830–834 (Sep. 1991).
Yarmush, M.L., et al., "Immunoadsorption: Strategies for Antigenic Elution and Production of Reusable Adsorbents," *Biotech. Prog.* 8:168–178 (May/Jun. 1992).
Pharmacia Fine Chemicals, "Chelating Sepharose 6B, For metal chelate affinity chromatography," pp. 1–7 (1982).

* cited by examiner

*Primary Examiner*—Deborah J. R. Clark
(74) *Attorney, Agent, or Firm*—Sterne, Kessler, Goldstein & Fox P.L.L.C.

(57) ABSTRACT

A method for purifying human or other alpha-1 proteinase inhibitor ($\alpha_1$-PI) from a solution (which may be derived from the milk of a transgenic animal expressing the $\alpha_1$-PI) which comprises contacting the solution with a cation exchange substrate under conditions sufficient to bind non-tg-$\alpha_1$-PI contaminants to the substrate while not substantially binding tg $\alpha_1$-PI to the substrate. Using the preferred embodiment, the purified tg $\alpha_1$-PI contains as little as 40 pg non-$\alpha_1$-PI-whey protein per mg total protein.

6 Claims, 2 Drawing Sheets

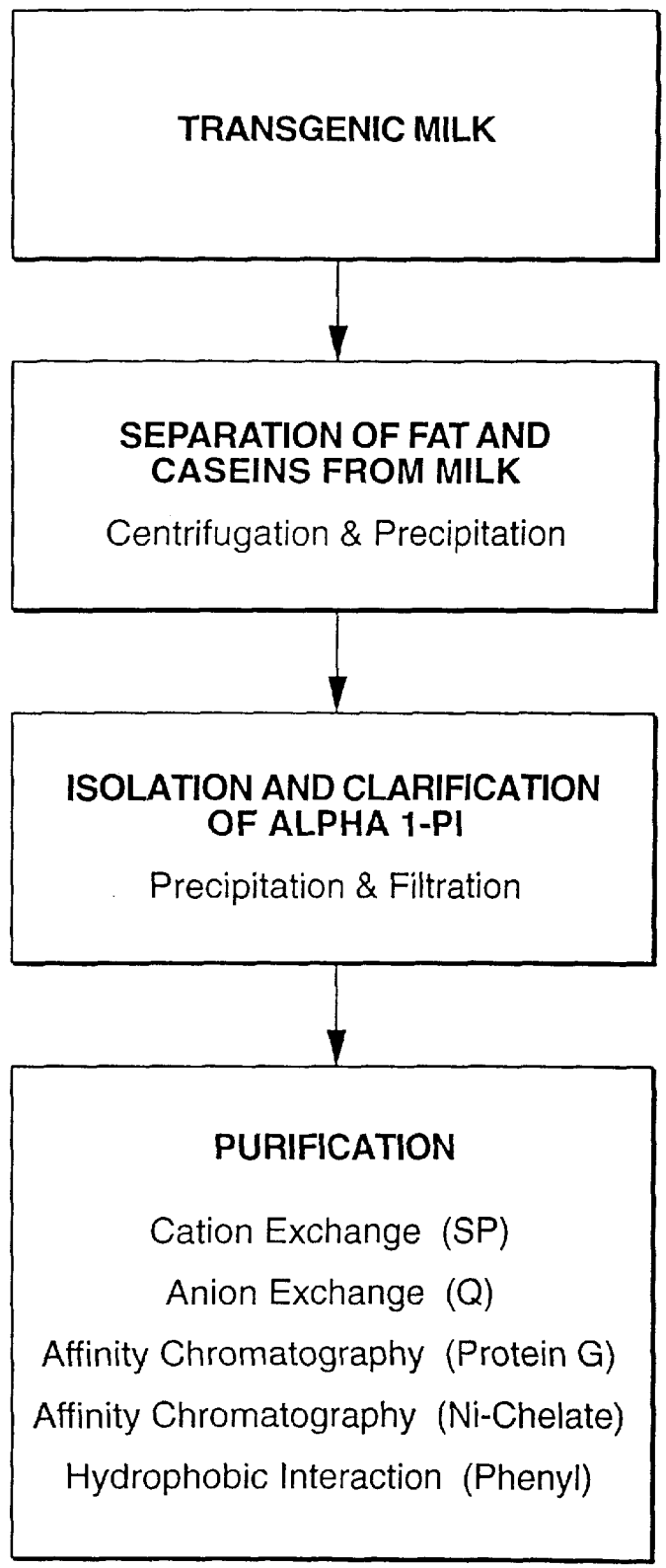
FIG._1

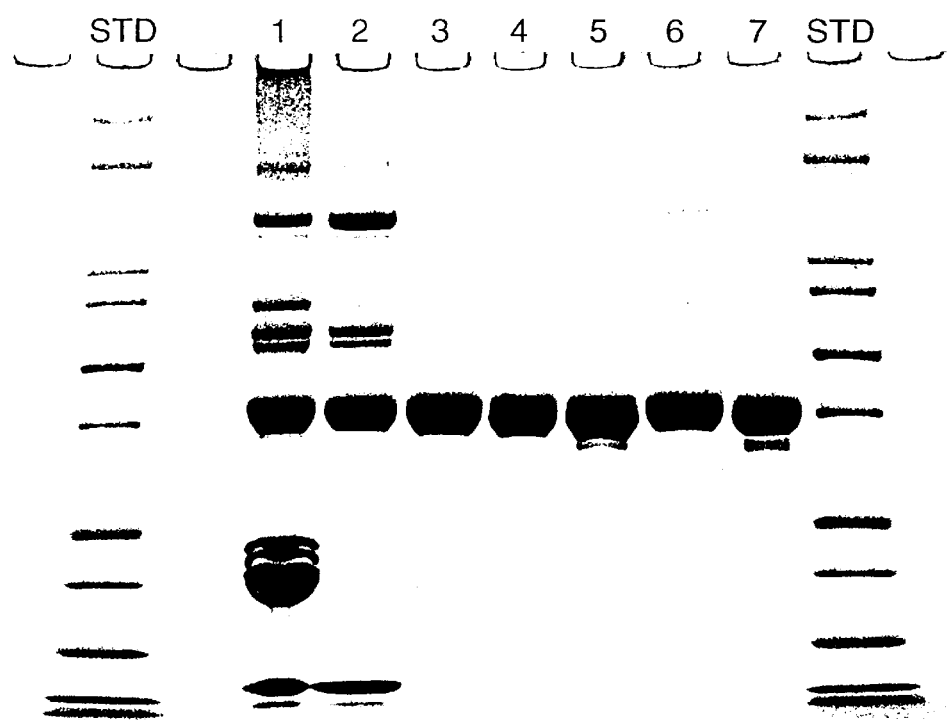
FIG._2
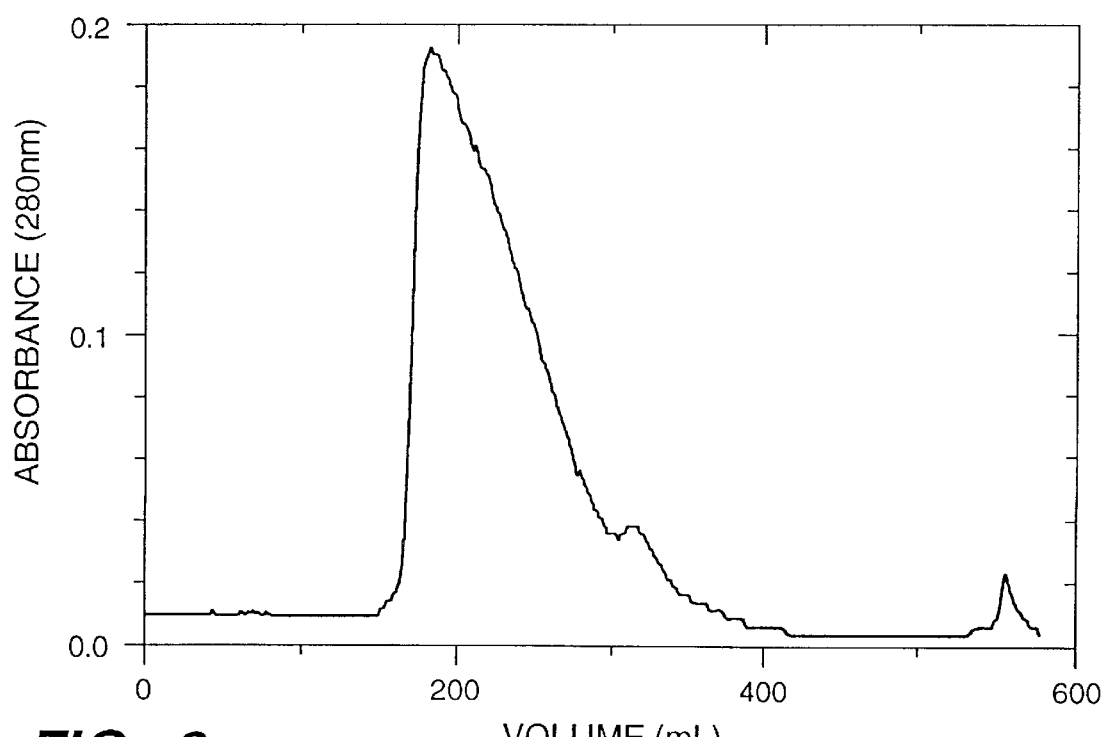
FIG._3

PURIFICATION OF ALPHA-1 PROTEINASE INHIBITOR

This application is a continuation of International Application No. PCT/GB96/02194, filed Sep. 6, 1996, now abandoned, which is a continuation of application No. 08/525,359, filed Sep. 7, 1995, now abandoned, which are all hereby incorporated by reference.

This invention concerns generally the purification of a therapeutically useful protein and specifically the purification to near homogeneity of alpha-1 proteinase inhibitor ($\alpha_1$-PI), especially transgenic human $\alpha_1$-PI from a non-human animal source.

Currently, $\alpha_1$-PI (also known as $\alpha_1$-antitrypsin inhibitor) derived from human plasma is commercially available (Prolastin® $\alpha_1$-PI, Bayer Corporation) to treat congenital deficiencies of the protein. Such plasma-derived $\alpha_1$-PI comprises about 85% $\alpha_1$-PI of total protein on a wt/wt basis. Human plasma as a source, however, has disadvantages, including a limited supply, and the potential of viral contamination. These disadvantages have prompted investigations into a variety of recombinant sources so that the existing patient population could be more fully treated and the number of indications expanded without the above disadvantages.

Recombinant human $\alpha_1$-PI has been produced in both *E. coli* and yeast (Courtney et al., 1984; Sleep et al., 1991), but the lack of post-translation glycosylation by the microorganisms has led to unacceptably high pharmacokinetic clearance rates. While the conventional solution to this problem is to transfect mammalian cells to make a recombinant form of the protein, this approach is too costly given the large dose of $\alpha_1$-PI needed for congenitally deficient patients (60 mg/kg/week).

Wright et al., 1991, describe transgenic sheep that express human $\alpha_1$-PI with mammalian-like glycosylation in their milk at up to 30 g/l. Wright et al. (1994), without giving details, further report having isolated $\alpha_1$-PI "of very high purity (>99%)". However, our initial studies demonstrated that the major obstacles in preparing a pharmaceutical grade preparation of this protein for clinical use would be in effectively eliminating the remaining sheep whey protein. A particular problem involved selectively eliminating sheep $\alpha_1$-PI from the transgenic human $\alpha_1$-PI.

The prior art reveals a number of methods which have been used to purify $\alpha_1$-PI. Bischoff et al. (1991) have isolated site-directed mutant $\alpha_1$-PI produced by *E. coli*. Their method consisted of chromatography over a silica-based anion exchange substrate, zinc-chelate chromatography, ammonium sulfate fractionation, and hydrophobic interaction chromatography. The resultant product was reported to be "of high purity as determined by PAGE under reducing conditions in the presence of SDS" (pp. 3468–3469). HPLC analysis of the product showed no contaminant at greater than 1%, the detection limit of the instrumentation.

Hoylaerts et al. (1986) have used a small scale immunoaffinity chromatography process to obtain non-glycosylated recombinant $\alpha_1$-PI which was about 80% pure. They also developed a large scale purification process for $\alpha_1$-PI which consisted of precipitation with poly(ethylene glycol), DEAE-Sepharose® chromatography, zinc-chelate chromatography, a kappa-chain-agarose chromatography step, a heparin-agarose chromatography step, and an aminohexyl-agarose chromatography step. The six step process yielded material which was greater than 95% pure.

However, the $\alpha_1$-PI isolated by Bischoff et al. and Hoylaerts et al. is non-glycosylated and therefore is of limited pharmacological use. Archibald et al. (1990) report characterization of transgenic human $\alpha_1$-PI produced in the milk of transgenic mice. Mistry et al. (1991) have developed a purification process for native, glycosylated sheep $\alpha_1$-PI which consists of ammonium sulfate precipitation, concanavalin A chromatography, anion exchange chromatography on a Mono Q® column, and preparative scale native-PAGE. A further step used was immunoadsorbant column chromatography to obtain a product which was greater than 98% pure as measured by SDS-PAGE.

However, even a purity of 98+% would be inadequate for parenteral drug use of $\alpha_1$-PI isolated from a non-human source. The potential immune response to contaminants necessitates a product of extremely high purity. It is thus of primary importance to discover a method which results in a product of the requisite purity for parenteral use.

Such a high level of purity requires a multistep process, with a high yield at each step. The prior art reveals anion exchange chromatography steps, fractionation steps using either poly(ethylene glycol) or ammonium sulfate, and immunoaffinity chromatography steps. Bollen et al. (1986) report a multistep process for purifying $\alpha_1$-PI which yields "highly purified" $\alpha_1$-PI with "trace contaminants". The Bollen process includes anion exchange, thiol exchange, heparin-affinity, and Zn-helate chromatography steps.

The use of an immobilized zinc affinity chromatography step for purification of $\alpha_1$-PI is detailed in the prior art. See, for example, Kurecki, et al., 1979. The use of cation exchange to purify a complex of native human $\alpha_1$-PI and proteinase-3 has been reported by Ballieux et al. (1993) The complex isolated by Ballieux et al. is too small to contain intact proteins, and is most likely a degradation product of the complexed proteins. The use of a cation exchange chromatography step in a scheme for purifying intact, native human $\alpha_1$-PI derived from plasma also was described by Lebing and Chen (1994).

We have prepared an essentially homogenous transgenic human alpha-1 proteinase inhibitor (tg $\alpha_1$-PI) which has a purity substantially greater than 99.99 g tg $\alpha_1$-PI/100 g total protein. This product is preferably prepared by subjecting a solution containing impure tg $\alpha_1$-PI to a series of chromatography steps comprising at least one cation exchange step. The preferred embodiment includes anion exchange, protein G affinity chromatography, immobilize nickel affinity chromatography, and hydrophobic interaction chromatography steps. Preferably, the contact with the cation exchange material (resin) is performed at about pH 5.5 with the salt concentration at or below about 10 mM. In the most preferred embodiment, the purified tg $\alpha_1$-PI includes less than 40 pg of protein other than casein, native sheep $\alpha_1$-PI, and tg $\alpha_1$-PI per mg total protein.

Preferred embodiments of the invention will now be described. The description refers to the accompanying drawings, in which:

FIG. 1 shows a block diagram of a process used to purify alpha-1 proteinase inhibitor ($\alpha_1$-PI).

FIG. 2 shows a non-reducing SDS-PAGE analysis of samples throughout the purification process. Gel was 4–20%, stained with Coomassie Blue G-250. Lanes: (1) defatted milk; (2) PEG step II; (3) SP Sepharose®; (4) Q Sepharose®; (5) Protein G Sepharose®; (6) Ni-IMAC; (7) Phenyl Sepharose®. Protein standards were (kDa) 200, 116, 97, 66, 55, 36, 31, 21.5, 14.4, and 6.

FIG. 3 shows a sample chromatogram for the Phenyl Sepharose® step showing the main peak with a trailing shoulder.

MATERIALS AND METHODS

Transgenic Sheep Milk Milk from transgenic sheep was supplied by Pharmaceutical Proteins, Ltd. (Edinburgh, UK).

All sheep were descendants of one transgenic male. In the milk of these sheep, the concentration of transgenic alpha-1 proteinase inhibitor (tg $\alpha_1$-PI) was 10–12 mg/ml. Approximately 85% of the undesired protein is casein (Table I). Casein is a mixture of mostly insoluble proteins present as a micellar suspension, giving milk its characteristic appearance (Wilkins and Velander, 1992). The remainder of the proteins are, by definition, whey protein. Whey proteins, which by the above definition exclude casein, comprise those proteins that have been synthesized by the mammary gland (e.g., $\alpha$-lactalbumin and $\beta$-lactoglobulin) and most serum proteins. Among the latter is endogenous $\alpha_1$-PI (i.e. sheep $\alpha_1$-PI). Because sheep $\alpha_1$-PI could copurify with the transgenic human $\alpha_1$-PI, its removal is of particular interest.

As used herein, "non-$\alpha_1$-PI-whey protein" means all protein present in milk except casein, native sheep $\alpha_1$-PI, and tg $\alpha_1$-PI. "Non-tg-$\alpha_1$-PI contaminants" means any protein component which is not tg $\alpha_1$-PI. "Transgenic alpha-1 proteinase inhibitor" means the translation product of any human $\alpha_1$-PI gene which has been introduced into any animal by the use of molecular biology techniques. As this is the result of manipulations of genetic material and subsequent expression, it is recognized that the molecular biology techniques used may result in mutated gene sequences or translation or post-translation products which have different composition from native, human plasma derived $\alpha_1$-PI. These different compositions are intended to be encompassed by the term "transgenic alpha-1 proteinase inhibitor."

Elastase Inhibition Assay The concentration of tg $\alpha_1$-PI relative to a human plasma standard was measured by the inhibition of porcine pancreatic elastase, with the chromogenic compound N-succinyl-ala-ala-ala-p-nitroanilide as substrate. A standard curve was prepared using reference human plasma. The extinction coefficient for tg $\alpha_1$-PI was taken to be 0.5 ml mg$^{-1}$ cm$^{-1}$.

Whey Protein ELISA Sheep whey protein concentrations were determined using a sandwich ELISA. The standard was a protein mixture obtained by processing control sheep milk through a cation-exchange chromatography column.

Purification of Transgenic $\alpha_1$-PI The purification process is outlined in FIG. 1. It consists of a series of steps each of which, individually, is carried out in accordance with standard techniques of protein purification. Particular steps in the purification sequence were selected from a myriad of possibilities of process steps and sequences to achieve a purification process which is effective and efficient. The process comprises an initial defatting step (by centrifugation), two precipitations with polyethylene glycol (PEG), and five chromatography steps: cation and anion exchange, immunoaffinity with immobilized Protein G, immobilized-metal affinity (IMAC) with nickel, and hydrophobic interaction (HIC) chromatography. As used herein when referring to the chromatography steps, "substrate" means any support material suitable for a chromatographic separation, where the support material is suitably modified to have a given selectivity. For example, immobilized metal affinity chromatography substrates are support materials which are modified with chelating groups which bind metals, which in turn selectively bind to proteins in solution.

This process has been characterized with respect to purity (by SDS-PAGE gels, Western blots, and whey protein ELISA) and yield. The gels are shown in FIG. 2; the other values may be found in Table II. Under non-reducing conditions, Western blotting shows that the high molecular weight band in the late process samples (as shown in FIG. 2) is a dimer of $\alpha_1$-PI. Occasionally, as in this case, a band appears beneath the $\alpha_1$-PI band. This is a breakdown product.

SDS-PAGE shows that after PEG precipitation and cation exchange, transgenic $\alpha_1$-PI (tg $\alpha_1$-PI) is the predominant protein present, with only a trace of albumin. Once this has been removed (by anion exchange chromatography), SDS-PAGE is of limited value in assessing purity. In contrast, the whey protein level decreases at every step, from $7.6 \times 10^8$ to 40 pg/mg, a reduction by a factor of $2 \times 10^7$. The overall yield is 44%.

TABLE I

Composition of Sheep Milk (%)

| | |
|---|---|
| Total solids | 19.3 |
| Fat | 7.4 |
| Casein | 4.6 |
| Whey protein | 0.9 |
| Lactose | 4.8 |
| Ash | 1.0 |

Taken from Jenness (1970).

TABLE II

Summary of Purification

| | Yield (%) | | Whey/$\alpha_1$-PI |
|---|---|---|---|
| Steps | Step | Overall | (pg/mg) |
| Milk | 100 | | $7.6 \times 10^8$ |
| Defatting | 90 | 90 | NA |
| PEG Step 1 | 75 | 68 | NA |
| PEG Step 2 | 95 | 65 | $5.6 \times 10^8$ |
| SP Sepharose ® | 85 | 55 | $6.8 \times 10^6$ |
| Q Sepharose ® | 85 | 47 | $2.1 \times 10^6$ |
| Protein G Sepharose ® | 102 | 48 | $1.1 \times 10^6$ |
| UF/DF | 103 | 49 | $8.7 \times 10^5$ |
| Ni-chelate | 95 | 47 | $5.6 \times 10^4$ |
| UF/DF | 106 | 50 | NA |
| Phenyl Sepharose ® | 87 | 44 | $4.0 \times 10^1$ |

Discussion of individual purification steps

The individual purification steps are summarized in Table II.

Selection of the Initial Purification Step Casein is preferably removed shortly after milking to allow sterile filtration of the whey. The most straightforward option is precipitation of the casein by some method. Possible precipitating agents are listed in Table III. Several of these agents were investigated with the goals of improving yield or the specificity for tg $\alpha_1$-PI. Precipitation with PEG proved to be superior to any of the alternatives listed in Table III. Two PEG precipitations were used, the first to precipitate casein, and the second to precipitate tg $\alpha_1$-PI. The tg $\alpha_1$-PI, once resolubilized, was substantially free of casein, PEG, and a number of whey proteins.

The following five chromatographic steps were designed to further reduce the amount of contaminating protein relative to tg $\alpha_1$-PI.

TABLE III

Agents Tested for Casein Precipitation

Polyethylene Glycol
Ammonium sulfate
Chymosin
High salt/ reducing conditions/ 60° C.

Cation Exchange We are not aware of any use of cation exchange chromatography for the purification of tg $\alpha_1$-PI in the prior art. Quite surprisingly, we found that cation exchange chromatography is an effective and useful part of a purification scheme. The isoelectric point of tg $\alpha_1$-PI is between 4 and 5. However, human $\alpha_1$-PI loses its activity below pH 5.0 (Glaser et al., 1977), so at stable pH, it does not bind to cation exchange resins. Nevertheless, more than 90% of the whey protein in the crude tg $\alpha_1$-PI obtained from PEG precipitation was removed during passage over a cation exchanger at pH 5.5. The major proteins removed were $\alpha$-lactalbumin and $\beta$-lactoglobulin. Below pH 5.5, tg $\alpha_1$-PI lost activity and bound to the matrix, reducing yield. At higher pHs, purification was less effective. Although in the best mode disclosed here we describe the use of SP-Sepharose® FF, it should be appreciated that other cation exchange substrates could be used, and the particular experimental conditions (e.g. pH, ionic strength) may vary with the substrate.

Anion Exchange The pH range 5.5–8.5 was investigated. The highest pH, 8.5, was the most effective in removing albumin, which otherwise tended to copurify with the tg $\alpha_1$-PI. The binding capacity was also highest at pH 8.5. The selectivity of ion exchange can vary with pH, so a second anion-exchange step was investigated in order to determine if other proteins would be removed at a different pH. Subsequent chromatography at pH 6.0 had no further effect on the whey protein level.

Immobilized Protein G Immunoglobulin G is a significant milk protein in sheep, being the dominant immunoglobulin (Hanson and Johansson, 1970). This protein appeared to carry through the purification cascade during early experiments; this step was inserted for its removal. Both Protein A and Protein G were evaluated. Protein A ordinarily binds sheep IgG poorly; binding can be increased in the presence of high salt. In this application, Protein G was superior to Protein A in reducing whey protein level. SDS-PAGE of the bound protein fraction confirmed that IgG was removed from the tg $\alpha_1$-PI.

As an alternative to chromatography over immobilized Protein G, thiophilic affinity chromatography was tested. Several thiophilic resins are marketed for antibody purification. Such a resin may be preferred to immobilized Protein G because (1) cost would be lower, (2) specificity to immunoglobulins in general (as opposed to just IgG) might be superior, and (3) the application buffer, normally containing ammonium sulfate, would be compatible with the HIC step.

Suitability was tested using Fractogel® EMD 650(S) AF-TA (EM Separations). Eluate from the anion-exchange step (FIG. 1) was applied in 0.8 M $(NH_4)_2SO_4$ at pH 7. SDS-PAGE of the bound fraction was consistent with immunoglobulin removal. The whey-protein level was reduced by a factor of 1.4. Essentially 100% yield was obtained for $(NH_4)_2SO_4$ concentrations of 0.8 and 1.2 M, with slightly higher whey protein clearance at the higher concentration. At 1.6 M $(NH_4)_2SO_4$, tg $\alpha_1$-PI bound weakly to the matrix, thereby reducing yield.

Immobilized-Metal Affinity Chromatography (IMAC) Immobilized-metal affinity chromatography was studied in detail for its usefulness in purification. Chelating Sepharose® FF (Pharmacia) was loaded with $Cu^{2+}$, $Zn^{2+}$, or $Ni^{2+}$. Testing was carried out on the eluate from SP Sepharose®, dialyzed into the starting buffer. This was applied to the metal-containing column. Bound species were eluted in an imidazole gradient.

As is the case for many proteins, binding was tightest to the copper and weakest to the zinc (Sulkowski, 1989). The copper, however, offered no specificity. Binding of tg $\alpha_1$-PI to the zinc-containing matrix was so weak that it was unsuitable. A few contrary claims exist in the literature (Bollen et al., 1986; Hoylaerts et al., 1986; Bischoff et al., 1991); it may be that only unglycosylated $\alpha_1$-PI will bind. In one case, the conditions used were manipulated to take advantage of extremely weak binding; that approach would not be applicable to large-scale operation (Kurecki et al., 1979).

In contrast to copper and zinc, and to our surprise, nickel immobilized on Chelating Sepharose® proved to be useful in separating tg $\alpha_1$-PI from whey proteins, particularly $\alpha$-lactalbumin. Both pH reduction and imidazole gradients were tested as elution methods. They appeared to be equivalent, although the imidazole offered more control over the separation.

Hydrophobic Interaction Chromatography Two hydrophobic interaction supports were evaluated; in turn, these were tested in both flow-through and binding modes. Transgenic $\alpha_1$-PI bound to Butyl-650M (TosoHaas) was difficult to elute with aqueous buffers. When this support was used in flow-through mode, yield was high, yet the purity improvement was modest (Table IV). Phenyl Sepharose® HP (Pharmacia) proved to be highly effective in reducing the whey protein level, at least when following several other steps. The presence of a small amount of EDTA improved the separation. Tg $\alpha_1$-PI eluted in a broad peak followed by a poorly-resolved shoulder (FIG. 3). The final improvement in purity was obtained by cutting out this shoulder, the yield was reduced from 100% to 87% in doing so.

TABLE IV

Conditions for Hydrophobic Interaction Chromatography

|  | Yield (%) | Whey/tg $\alpha_1$-PI (ng/mg) |
| --- | --- | --- |
| Ni eluate |  | 56 |
| Butyl 650M[1] | 80 | 12 |
| Phenyl (− EDTA)[2] | 77 | 1.6 |
| Phenyl (+ EDTA)[3] | 100 | 0.43 |

Notes:
[1]Solid $(NH_4)_2SO_4$ was added to eluate from the Ni-IMAC column for a concentrator of 0.5 M.
[2]The feed concentration of $(NH_4)_2SO_4$ was 1.5 M. Product was collected in a gradient to 0 M $(NH_4)_2SO_4$, collecting all of the major peak.
[3]Same as [2], but the buffers contained 1 mM EDTA.

Detailed Process Description for Best Mode

Defatting and PEG Precipitation Whole milk from transgenic sheep was defatted by centrifugation. Casein was removed by a two-step poly(ethylene glycol) (PEG) precipitation. After the first addition of PEG, the precipitate was separated from the supernatant by centrifugation. More PEG was then added to the supernatant to precipitate the tg $\alpha_1$-PI. The precipitate was then redissolved in loading buffer, preparatory to the next step.

Cation Exchange A column of SP-Sepharose® FF (Pharmacia) was equilibrated with 50 mM tris-acetate, 10 mM NaCl, pH 5.5. The column volume should be at least 6% of the starting milk volume. The redissolved, crude $\alpha_1$-PI from above was adjusted to pH 5.5 and applied to the column at 50–60 cm/hr. The flow-through peak was collected, and the bound contaminants stripped off the column with 1–2 M NaCl.

Anion Exchange Q Sepharose® FF (Pharmacia) was equilibrated with 50 mM tris, 30 mM acetic acid, 10 mM NaCl, pH 8.5. The flow-through from the cation-exchange step was adjusted to pH 8.5 and applied to the column at up to 100 cm/hr. The column binding capacity for $\alpha_1$-PI was 25–30 mg/ml. Bound tg $\alpha_1$-PI was eluted in a 30-columnvolume gradient in NaCl concentration from 10 to 200 mM. Protein eluting only between 75 and 155 mM NaCl (measured at the column inlet) was collected.

Protein-G Affinity Protein-G-Sepharose® FF (Pharmacia) was equilibrated with 50 mM glycine, 250 mM NaCl, pH 8.0. NaCl was added, at 100 mM, to the eluate from Q Sepharose®, and the pH was then adjusted to 8.0 with HCl. This was passed over the column at 25 cm/hr. The flow-through peak was saved; bound protein was stripped off with a buffer containing 50 mM each glycine and acetic acid, at pH 2.1.

Immobilized-Metal Affinity

Column Preparation Chelating Sepharose® FF (Pharmacia), which contains immobilized imninodiacetic acid (IDA) as the chelating group, was washed extensively with distilled water. Buffer A (0.6% $NiSO_4 x 6H_2O$, 10 mM acetic acid, pH 6.0) was used to load the column with nickel. A green front moved down the column as it was loaded, and before the front was a zone of low pH. Loading was complete when the outlet pH returned to 6.0 and nickel was confirmed in the column outlet by precipitation in 2 M $Na_2CO_3$. Loosely bound nickel was removed by washing with buffer B (250 mM acetic acid, pH 5.0, 150 mM NaCl). The column was then equilibrated with buffer C (20 mM phosphate, pH 8.0, 500 mM NaCl) before use.

Column Operation The eluate from the Protein-G step was diafiltered against buffer C and applied to the equilibrated column at 50 cm/hr. Up to 15 g/L $\alpha_1$-PI could be loaded. Tris buffer interfered with binding, but concentrations below 2.3 mM could be tolerated. After the flow-through peak emerged, the $\alpha_1$-PI was eluted in a 20-column-volume gradient from buffer C to buffer D (Buffer C+20 mM imidazole).

Reuse and Regeneration The column was stripped of remaining protein with 100 mM imidazole, or completely stripped of both protein and nickel with buffer E (50 mM EDTA, pH 7.0, 500 mM NaCl).

Hydrophobic Interaction Eluate from the Ni-IMAC step was diafiltered into 50 mM tris-acetate buffer, pH 7.5. Solid $(NH_4)_2SO_4$ was added to a concentration of 1.5 M; EDTA was added to 1 mM. After a 30 min incubation at room temperature, the $\alpha_1$-PI solution was applied, again at room temperature, to Phenyl Sepharose® HP (Pharmacia) equilibrated in the tris/acetate/$(NH_4)_2SO_4$/EDTA buffer at 60 cm/hr. Loading was between 10 and 15 mg/ml. A descending gradient in $(NH_4)_2SO_4$ concentration to 0 M (other buffer components held constant) was used to elute the $\alpha_1$-PI. The $\alpha_1$-PI eluted in a broad peak (FIG. 3), followed by a small shoulder. The main peak was collected, ending with the inflection point defining the beginning of the shoulder.

Discussion

The extraordinary purity required for tg $\alpha_1$-PI made the development of a purification process particularly challenging. Conventional tools for assessing purity, such as specific activity, SDS-PAGE gels, and Western blots, were useful only for the initial stages of purification. Specific activity has a mean error of a few percent and is thus unsuitable for measuring trace contaminant levels. SDS-PAGE sensitivity with coomassie blue staining is 1–10 ng. Under ideal conditions, contaminants at the 0.04% level can be detected (assuming 25 μg loading). This is, however, a very heavy load, and the $\alpha_1$-PI would appear as a large, broad band that could obscure other proteins. Silver staining is more sensitive, but to both $\alpha_1$-PI and contaminants. Western blots are not quantitative (different proteins stain differently). A representative sensitivity might be 100 pg (Bio-Rad (1991) p. 39). If 25 μg is blotted, one can pick up contaminants at the 4 ppm level. The ELISA assay for sheep whey proteins provided a broad gauge of purity without specifically identifying contaminants. The sensitivity of the ELISA assay as performed is estimated to be about 0.16 ng/ml.

In addition, tg $\alpha_1$-PI proved to be a heterogeneous protein. In three purification steps, where gradients were used for elution (anion-exchange, Ni-IMAC, and HIC), the tg $\alpha_1$-PI eluted as a group of two or more poorly-resolved peaks. Typically, no specific contaminants could be identified as having been removed at a single step. Also, past the anion-exchange step, contaminant peaks were too small to be visible.

In light of these considerations, the successful strategy was to use a series of chromatographic steps based on distinct separation mechanisms. To maintain reasonable overall yield, each individual step would have to have a high yield. This multi-step process succeeded in reducing whey proteins to a nonimmunogenic level.

An ELISA specific to sheep $\alpha_1$-PI suggests that sheep $\alpha_1$-PI could be separated from 1 transgenic protein (Table V), but the residual level may still be immunogenic. If so, an immunoaffinity step may be necessary to remove this contaminant. With this addition, the process described here can provide the basis for continuing preclinical development of $\alpha_1$-PI from transgenic sheep.

TABLE V

Separation of Sheep $\alpha_1$-PI from tg $\alpha_1$-PI

| Process Step | Sheep $\alpha_1$-PI Level (ng/mg) |
| --- | --- |
| SP Eluate | 230–690 |
| Q Eluate | 50 |
| Protein G | 61 |
| Ni-IMAC | 6.2 |

Given the above disclosure, it is thought that variations will occur to those skilled in the art. Accordingly, it is intended that the above disclosure should be construed as illustrative and the scope of the invention should be limited only by the claims contained herein.

References

Bio-Rad, *Protein Blotting: A Guide to Transfer and Detection* (1991).

Ballieux, B. E. P. B, et al., Isolation of a Protein Complex from Purulent Sputum Consisting of Proteinase-3 and $\alpha_1$-Antitrypsin Reactive with Anti-Neutrophil Cytoplasmic Antibodies, *J. Immunol. Meth.*, 159:63–70 (1993).

Bischoff, R. et al., Purification and Biochemical Characterization of Recombinant Alpha-1-Antitrypsin Variants Expressed in *Escherichia coli*, *Biochemistry* 30: 3464–3472 (1991).

Bollen, A. J. et al., Alpha-1-Antiprotease Purification, U.S. Pat. No. 4,629,567 (1986).

Courtney, M. et al., High-Level Production of Biologically Active Human Alpha-1-Antitrypsin in *Escherichia coli*, *Proc. Nail. Acad. Sci. U.S.A.* 81: 669–673 (1984).

Glaser, C. B. et al., Low pH Stability of Alpha-1-Antitrypsin, *Biochim. Biophys. Acta* 491: 325–330 (1977).

Hanson, L. A. and Johansson, B. G., Immunological Studies of Milk, in *Milk Proteins: Chemistry and Molecular Biology*, vol. 1, H. A. McKenzie, ed., Academic, New York (1970).

Hoylaerts, M. et al., High-Level Production and Isolation of Human Recombinant Alpha-1-Proteinase Inhibitor in Yeast, *FEBS Lett.* 204: 83–87 (1986).

Jenness, R., Protein Composition of Milk, in *Milk Proteins: Chemistry and Molecular Biology*, vol. 1, H. A. McKenzie, ed., Academic, New York (1970).

Kurecki, T. et al., Purification of Human Plasma Alpha-2 Macroglobulin and Alpha-1 Proteinase Inhibitor Using Zinc Chelate Chromatography, *Anal. Biochem.* 99: 415–420 (1979).

Lebing, W. R. and Chen, S., U.S. patent application Ser. No. 08/295,119, Purification of Alpha-1 Proteinase Inhibitor Using Novel Chromatographic Separation Conditions (filed Aug. 24, 1994).

Mistry, R. et al., Isolation and Characterization of Sheep $\alpha_1$-Proteinase Inhibitor, *Biochem. J.* 273:685–690 (1991).

Sleep, D. et al., *Saccharomyces cerevisiae* Strains that Overexpress Heterologous Proteins, *Bio/Technol.* 9: 183–187 (1991).

Sulkowski, E., The Saga of IMAC and MIT, *BioEssays* 10: 170–175 (1989).

Wilkins, T. D. and Velander, W., Isolation of Recombinant Proteins from Milk, *J. Cell. Biochem.* 49: 333–338 (1992).

Wright, G. et al., High Level Expression of Active Alpha-1-Antitrypsin in the Milk of Transgenic Sheep, *Bio/Technol.* 9: 830–834 (1991).

Wright, G. et al., Protein Separation from Transgenic Milk, *J. Chem. Technol. Biotechnol.* 59:110 (1994).

What is claimed is:

1. A method of purifying alpha-1-proteinase inhibitor ($\alpha_1$-PI) from a solution comprising $\alpha_1$-PI and non-$\alpha_1$-PI contaminants, the method comprising:
   (a) conducting cation exchange chromatography under conditions sufficient to bind the non-$\alpha_1$-PI contaminants to the cation exchange substrate while not binding the $\alpha_1$-PI; and
   (b) conducting immobilized nickel affinity chromatography under conditions sufficient to bind $\alpha_1$-PI to the nickel affinity substrate, wherein the $\alpha_1$-PI is purified to a level of greater than 99.99 g $\alpha_1$-PI/100 g total protein.

2. A method as claimed in claim 1, wherein the contact with the cation exchange substrate is at ionic strength less than about 0.01 and at a pH between about 5 and 6.

3. A method as claimed in claim 1, wherein the solution is derived from a non-human mammal expressing a transgene encoding $\alpha_1$-PI.

4. A method as claimed in claim 3, wherein the transgene encoding $\alpha_1$-PI is expressed in the mammary gland of a transgenic non-human mammal.

5. A method as claimed in claim 4, wherein the $\alpha_1$-PI is human $\alpha_1$I-PI.

6. A method as claimed in claim 5, wherein the purified $\alpha_1$-PI has less than about 40 pg non-$\alpha_1$-PI-whey protein/mg total protein.

* * * * *